US010238321B2

(12) United States Patent
Kahlman et al.

(10) Patent No.: US 10,238,321 B2
(45) Date of Patent: Mar. 26, 2019

(54) USE OF A BARRIER CONTACT MEDIUM FOR CHEMO-CHEMO-OPTICAL SENSORS IN TRANSCUTANEOUS APPLICATIONS

(71) Applicant: KONINKLIJKE PHILIPS N.V., Eindhoven (NL)

(72) Inventors: Josephus Arnoldus Henricus Maria Kahlman, Tilburg (NL); Nicolaas Lambert, Waalre (NL); Hans Willem Van Kesteren, Eindhoven (NL)

(73) Assignee: KONINKLIKE PHILIPS N.V., Eindhoven (NL)

( * ) Notice: Subject to any disclaimer, the term of this patent is extended or adjusted under 35 U.S.C. 154(b) by 600 days.

(21) Appl. No.: 14/892,217

(22) PCT Filed: Jun. 6, 2014

(86) PCT No.: PCT/EP2014/061811
§ 371 (c)(1),
(2) Date: Nov. 19, 2015

(87) PCT Pub. No.: WO2014/195451
PCT Pub. Date: Dec. 11, 2014

(65) Prior Publication Data
US 2016/0081605 A1 Mar. 24, 2016

(30) Foreign Application Priority Data

Jun. 6, 2013 (EP) .................................... 13170728

(51) Int. Cl.
*A61B 5/1455* (2006.01)
*A61B 5/145* (2006.01)
*A61M 16/00* (2006.01)
(Continued)

(52) U.S. Cl.
CPC .......... *A61B 5/14556* (2013.01); *A61B 5/145* (2013.01); *A61B 5/1455* (2013.01);
(Continued)

(58) Field of Classification Search
CPC ... A61B 5/145; A61B 5/1455; A61B 5/14539; A61B 5/14556; A61B 5/1477
See application file for complete search history.

(56) References Cited

U.S. PATENT DOCUMENTS

| 4,220,158 A | 9/1980 | Delpy et al. |
| RE31,879 E * | 5/1985 | Lubbers ............... G01N 21/643 422/562 |

(Continued)

FOREIGN PATENT DOCUMENTS

| EP | 1965198 A1 | 3/2008 |
| WO | 02056023 A1 | 7/2002 |
| WO | 2013064313 A1 | 5/2013 |

OTHER PUBLICATIONS

Kocincova, "New pH Sensitive Sensor Materials. Luminescent Fiber-Optic Dual Sensors for Non-Invasive and Simultaneous Measruement of pH and pO2 (Dissolved Oxygen) in Biological System", PhD Thesis, University of Regensburg, 2007, 161 Page Document.

(Continued)

*Primary Examiner* — Eric Winakur
*Assistant Examiner* — Chu Chuan (J J) Liu
(74) *Attorney, Agent, or Firm* — Michael W. Hass

(57) ABSTRACT

The present invention relates to a chemo-optical sensor unit for transcutaneous measurement of a concentration of a gas, comprising: at least one sensing layer adapted to be irradiated with a predetermined radiation; and at least one gas-permeable layer adjacent to one side of the at least one sensing layer, adapted to pass gas whose concentration is to be measured through the gas-permeable layer towards the sensing layer; wherein said chemo-optical sensor unit is adapted to operate with a contact medium between the gas-permeable layer and the skin, wherein said contact medium comprises a barrier layer which is gas-permeable and impermeable to water and ions; and wherein the chemo- (Continued)

optical sensor unit is adapted to measure an optical response of the at least one sensing layer, whose optical response depends on the concentration of the gas. The present invention also relates to a system comprising such a chemo-optical sensor, as well as to a method for conditioning a chemo-optical sensor unit for measuring a concentration of a gas and a thereby obtainable conditioned sensor.

17 Claims, 1 Drawing Sheet

(51) Int. Cl.
    *A61B 5/1477* (2006.01)
    *G01N 33/00* (2006.01)

(52) U.S. Cl.
    CPC ....... *A61B 5/1477* (2013.01); *A61M 16/0069* (2014.02); *G01N 33/004* (2013.01)

(56) References Cited

U.S. PATENT DOCUMENTS

| | | |
|---|---|---|
| 5,114,676 A | 5/1992 | Leiner et al. |
| 6,602,716 B1 | 8/2003 | Klimant |
| 2001/0029326 A1 | 10/2001 | Diab et al. |
| 2003/0003593 A1 | 1/2003 | Wallach |
| 2009/0004751 A1* | 1/2009 | Leiner .................. G01N 21/783 436/133 |
| 2009/0216097 A1 | 8/2009 | Wilson et al. |
| 2011/0104021 A1* | 5/2011 | Curello .................. B01D 53/22 422/240 |

OTHER PUBLICATIONS

Schaferling, "The Art of Fluorescence Imaging With Chemical Sensors", Angewandte Chemie International Edition, vol. 51, No. 15, 2012, p. 3532-3554.

Mills et al, "Fluorescent Carbon Dioxide Indicators", XP055085367, University of Strathclyde, 2005, p. 1-43.

Kawabata et al, "Fiber-Optic Sensor for Carbon Dioxide With a pH Indicator Dispersed in a Poly(Ethylene Glycol) Membrane", Analytica Chimica Acta, 1989, p. 223-229.

Anonymous, "CO2 Sensors", Presens Products, XP0992715621, Retrieved From the Internet: http://www.presens.de/products/brochures/category/sensor-probes/brochure/co2-sensors.html, Oct. 28, 2013, 5 Page Document.

\* cited by examiner

USE OF A BARRIER CONTACT MEDIUM FOR CHEMO-CHEMO-OPTICAL SENSORS IN TRANSCUTANEOUS APPLICATIONS

CROSS-REFERENCE TO PRIOR APPLICATIONS

This application is the U.S. National Phase application under 35 U.S.C. § 371 of International Application Serial No. PCT/EP2014/061811, filed on Jun. 6, 2014, which claims the benefit of European Application Serial No. 13170728.3, filed on Jun. 6, 2013. These applications are hereby incorporated by reference herein.

FIELD OF THE INVENTION

The present invention relates to a chemo-optical sensor unit for transcutaneous measurement of a concentration of a gas, comprising: at least one sensing layer adapted to be irradiated with a predetermined radiation; and at least one gas-permeable layer adjacent to one side of the at least one sensing layer, adapted to pass gas whose concentration is to be measured through the gas-permeable layer towards the sensing layer; wherein said chemo-optical sensor unit is adapted to operate with a contact medium between the gas-permeable layer and the skin, wherein said contact medium comprises a barrier layer which is gas-permeable and impermeable to water and ions; and wherein the chemo-optical sensor unit is adapted to measure an optical response of the at least one sensing layer, whose optical response depends on the concentration of the gas. The present invention also relates to a system comprising such a chemo-optical sensor, as well as to a method for conditioning a chemo-optical sensor unit for measuring a concentration of a gas and a thereby obtainable conditioned sensor.

BACKGROUND OF THE INVENTION

Neuromuscular disease, chronic obstructive pulmonary disease (COPD) and obese hypoventilation patients often suffer from chronic respiratory failure. Said patients need regular treatment of their respiratory failure at home. Hypoxemic patients are treated by oxygen therapy (mostly without ventilator support), while treatment by Invasive Ventilation (IV) and Non Invasive Ventilation (NIV) with environmental air helps bringing the high carbon dioxide ($CO_2$) blood gas level of hypercapnic patients back to an acceptable level. The efficacy of the ventilation is checked by measuring the base-line and the trends in the arterial oxygen and carbon dioxide levels during nocturnal NIV.

Arterial blood gas measurements form the golden standard. Before starting ventilation treatment at home, patients stay at the hospital to optimize ventilator settings and monitor arterial blood gas values. Depending on disease severity and stability, patients have to return more or less regularly to the hospital for checks. A respiratory nurse can also visit the patient at home to check the ventilator and to install equipment that enables non-invasive monitoring of blood gas partial pressures. At home, blood gas levels are monitored typically during a night and data are stored together with ventilator and respiratory data for later analysis at the hospital.

The state of the art in non-invasive blood oxygenation monitoring, is by measuring the arterial oxygen saturation, which relates to the partial oxygen pressure via the oxygen dissociation curve. Pulse oximetry ($SpO_2$) is an optical method for non-invasive monitoring of arterial oxygen saturation in a patient and has become one of the most commonly used technologies in clinical practice. Pulse oximetry is a reasonably low cost technology and is easy to use. It is the preferred method for blood oxygenation monitoring at home.

The state of the art in non-invasive monitoring of the partial pressure of $CO_2$ is by means of capnography or by transcutaneous $CO_2$ ($PtcCO_2$) monitoring. For intubated patients with a healthy lung the end tidal $CO_2$ ($etCO_2$) value obtained by capnography offers a good indication of the arterial $CO_2$ value. However, in case of non-invasive ventilation where air leaks between mask and face are usually present and the patients have severe respiratory diseases capnography is often not a reliable method. In most hospitals a combination is used of capnography for trend monitoring and analysis of an arterial blood sample to obtain an occasional accurate value.

Transcutaneous $CO_2$ monitoring is not disrupted by air-leaks and respiratory diseases but requires trained personal to obtain reliable values and shows some inaccuracy due to variation in skin properties among adults. At home $CO_2$ blood gas monitoring is less frequently used than oximetry despite its high relevance for patients receiving ventilation.

Current transcutaneous $CO_2$ sensors are all based on a 40 year old concept of (i) a thermostatically controlled heater to increase blood perfusion and gas-permeability of the skin; (ii) a fluid layer between skin and sensor membrane; (iii) a gas-permeable membrane covering the sensor; (iv) an electrolyte solution between membrane and sensor; (v) a sensor comprising an electrochemical pH sensor and reference electrode; and (v) an algorithm to compensate for temperature effects and skin metabolism.

EP 1 965 198 A1 describes a device for determining $CO_2$ in gaseous or liquid samples comprising a polymer matrix and an indicator embedded in the polymer matrix, wherein the indicator comprises a pH sensitive dye and a metal cation complex, wherein an anion of the pH-sensitive dye and the metal cation form a salt which is soluble in the polymer matrix.

A further example of a prior art chemo-optical sensor for transcutaneous application is depicted in FIG. 1, wherein on top of an optical transparent carrier material two layers of "silicon rubber-like" gas-permeable materials are deposited The first layer—the sensing layer—comprises a mixture of two luminescent dyes in a lipophilic phase transfer agent within a hydrophobic polymer, namely a reference dye having a long luminescent life-time and a pH-sensitive indicator dye having a short luminescent life-time. A second membrane layer comprises light reflecting material ($TiO_2$) particles and prevents ion transport to and from the sensing layer. $CO_2$ gas typically diffuses through said membrane into the first (sensing) layer and changes the pH, which in turn modifies the luminescence from the indicator dye. By using a dual life-time referencing technique, which effectively measures the time response of modulated light excitation, the percentage of $CO_2$ gas can be calculated.

The lipophilic phase transfer agent also serves as chemical buffer material to provide water for the production of carbonic acid. However, osmotic imbalance at the site of application of the sensor, e.g. in a contact zone with a contact medium, may initiate molecular perturbations such as water transport in the sensor or out of the sensor, which may lead to unwanted sensitivity changes of the sensor, thus requiring a calibration or re-calibration of the sensor.

In consequence, there is a need for the development of an improved chemo-optical sensor for transcutaneous applications, in which no sensitivity changes due to molecular perturbations occur.

OBJECTS AND SUMMARY OF THE INVENTION

The present invention addresses these needs and provides means and methods for effectively measuring the concentration of gas, in particular of $CO_2$ in an osmotically unbalanced environment such as the skin. The above objective is in particular accomplished by a chemo-optical sensor unit for transcutaneous measurement of a concentration of a gas, comprising: at least one sensing layer adapted to be irradiated with a predetermined radiation; and at least one gas-permeable layer adjacent to one side of the at least one sensing layer, adapted to pass gas whose concentration is to be measured through the gas-permeable layer towards the sensing layer; wherein said chemo-optical sensor unit is adapted to operate with a contact medium between the gas-permeable layer and the skin, wherein said contact medium comprises a barrier layer which is gas-permeable and impermeable to water and ions; and wherein the chemo-optical sensor unit is adapted to measure an optical response of the at least one sensing layer, whose optical response depends on the concentration of the gas. The inventors provide the surprising solution that the use of a contact medium comprising a barrier layer which is gas-permeable and impermeable to water and ions effectively reduces or diminishes molecular disturbances such as water or ion transport in or out of the chemo-optical sensor unit and between the chemo-optical sensor unit and a contact medium such that no sensitivity changes during gas measurement, e.g. during the measurement of $CO_2$, occur. Thus, when the chemo-optical sensor unit according to the present invention is attached to a person's skin via a contact medium that is arranged between the at least one gas permeable layer and the skin, gasses present in the skin, for instance $O_2$ or $CO_2$, pass the gas permeable layer into a sensing layer as long as the gas partial pressure in the skin is higher than the gas partial pressure in the chemo-optical sensor unit. Due to presence of the barrier layer, which may comprise hydrophobic liquids, an osmotically inert environment may be provided which allows for the effective detection of the concentration of $O_2$ or $CO_2$ without the need for any additional calibration steps and without fearing a progressive falsification or invalidity of the measured values due to an influence of water influx to the sensing layer.

In a preferred embodiment of the present invention, the contact medium is biocompatible and optionally also thermally conductive.

In a further preferred embodiment of the present invention, the barrier layer as mentioned above comprises a hydrophobic compound.

In another preferred embodiment, said hydrophobic compound is a hydrophobic liquid.

In yet another preferred embodiment of the present invention said hydrophobic compound or hydrophobic liquid is a hydrocarbon, fluor or silicon containing oil, an organosilicone, or a soft rubber or gel.

In a particularly preferred embodiment of the present invention said hydrophobic liquid is an edible oil, or a low melting edible wax, preferably cocoa butter, a crude oil derivate, such as paraffin oil or soft paraffin wax, a silicone oil or silicone wax or a perfluoro oil.

In yet another preferred embodiment said at least one gas-permeable layer and/or said at least one sensing layer comprises a silicon rubber.

In a further preferred embodiment of the present invention, said barrier layer is present in said chemo-optical sensor unit in such a thickness that the optical response is stable when the chemo-optical sensor is in contact with said contact medium having a constant gas concentration.

In another preferred embodiment of the present invention said sensing layer comprises luminescent material and said gas-permeable layer is adapted to prevent light from passing through the gas-permeable layer.

It is particularly preferred that the chemo-optical sensor is a transcutaneous sensor unit for measuring blood gas concentration, preferably gas concentrations of $O_2$ and/or $CO_2$, more preferably gas concentration of $CO_2$.

In yet another preferred embodiment of the present invention the chemo-optical sensor unit as mentioned herein above further comprises:

at least one light source adapted to irradiate the sensing layer, and optionally a light guiding structure connected to the light source; and at least one detection device adapted to detect the optical response of the sensing layer, and optionally a light guiding structure connected to the detection device, wherein at least one of the light source, light guiding structure and/or the detection device are preferably detachably connected to the chemo-optical sensor unit.

In a further aspect, the present invention relates to a system for patient monitoring and/or ventilation of a patient, comprising a chemo-optical sensor unit as defined herein above, a ventilation device and/or a monitoring device.

In a further aspect the present invention relates to a method for conditioning a chemo-optical sensor unit for transcutaneous measurement of a concentration of a gas, comprising: at least one sensing layer adapted to be irradiated with a predetermined radiation; and at least one gas-permeable layer adjacent to one side of the at least one sensing layer, adapted to pass gas whose concentration is to be measured through the gas-permeable layer towards the sensing layer; wherein said chemo-optical sensor unit is adapted to operate with a contact medium between the gas-permeable layer and the skin, wherein said contact medium comprises a barrier layer which is gas-permeable and impermeable to water and ions; and wherein the chemo-optical sensor unit is adapted to measure an optical response of the at least one sensing layer, whose optical response depends on the concentration of the gas, the method comprising contacting said chemo-optical sensor unit with a contact medium comprising a barrier layer which is gas-permeable and impermeable to water and ions. In a preferred embodiment said contact medium is a contact medium as defined herein above.

In yet another aspect the present invention relates to a conditioned chemo-optical sensor unit for transcutaneous measurement of a concentration of a gas obtainable by the method for conditioning as defined herein above.

DETAILED DESCRIPTION OF THE EMBODIMENTS

Figure 1:
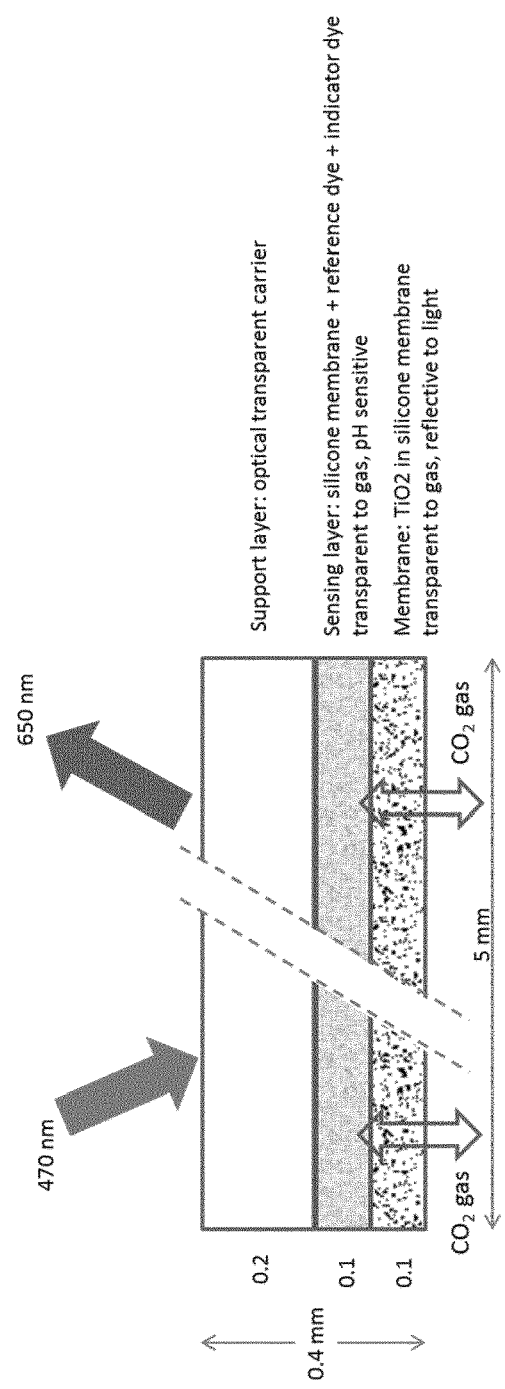
FIG. 1 shows the principles of a chemo-optical sensor for transcutaneous application. The FIGURE depicts a chemo-optical sensor comprising a support layer with an optical transparent carrier, a sensing layer comprising a silicone membrane, a reference dye and an indicator dye, which is transparent to gas and pH sensitive, as well as a layer comprising $TiO_2$ in a silicone membrane, which is transparent to gas and reflective to light. The chemo-optical sensor may, for example, be excited at 470 nm (blue-green LED) and the luminescence may be detected from indicator and reference dyes in the range of 500 to 700 nm (red). The reference dye has a slow response and the luminiphores may, for example, be packed in spheres to protect them from $O_2$. The indicator dye has a fast response and it is primary sensitive to $H^+$ (pH), leading to an decrease of the amplitude and a yellow coloring under white light illumination due to pH decrease caused by $CO_2$ increase. The frequency of the illumination light intensity modulation is chosen such that a phase shift at about 45° is obtained.

The present invention relates to a chemo-optical sensor unit for transcutaneous measurement of a concentration of a gas.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As has been set out above, the present invention concerns in one aspect a chemo-optical sensor unit for transcutaneous measurement of a concentration of a gas, comprising: at least one sensing layer adapted to be irradiated with a predetermined radiation; and at least one gas-permeable layer adjacent to one side of the at least one sensing layer, adapted to pass gas whose concentration is to be measured through the gas-permeable layer towards the sensing layer; wherein said chemo-optical sensor unit is adapted to operate with a contact medium between the gas-permeable layer and the skin, wherein said contact medium comprises a barrier layer which is gas-permeable and impermeable to water and ions; and wherein the chemo-optical sensor unit is adapted to measure an optical response of the at least one sensing layer, whose optical response depends on the concentration of the gas.

The term "concentration of a gas" relates to the amount of gas arriving at the chemo-optical sensor due to diffusion from zones or sectors to be measured. A "gas" may be any gaseous material. It is preferred that the gas is a biologically produced or biologically active or relevant gas. Examples of such gases are $O_2$, $CO_2$, CO, $N_2$, $NH_3$, NO, $H_2S$. It is preferred that the gas whose concentration should be measured is $O_2$ and/or $CO_2$. It is particularly preferred that the gas whose concentration should be measured is $CO_2$.

The term "sensing layer" as used herein refers to a layer which may be irradiated or excited and which may subsequently generate a light of a different wavelength due to the excitation of an optically reactive material, e.g. luminescence such as fluorescence, as optical response, wherein the intensity of the generated light depends on the concentration of gas molecules present in or dissolved in the sensing layer. The measurement of the optical response, e.g. luminescence such as fluorescence, of a certain intensity and wavelength, allows to calculate the gas concentration in the sensing layer, e.g. being diffusing or having diffused into the sensing layer from deeper layers such as the skin. This measurement may further allow a calculation of the concentration of such gas in the sector to be measured, e.g. in the sector of the skin on which the chemo-optical sensor is placed.

The sensing layer may be composed of filler material which is passable for gas molecules. An example of such filler material is silicone rubber material. In a preferred embodiment, the sensing layer may thus comprise silicone rubber or essentially consist of silicon rubber material. The sensing layer may further comprise compounds such as water or chemical buffers. The sensing layer may accordingly be buffered at a specific pH or comprise a certain amount of protons and/or hydroxide ions, e.g. have a certain pH. The pH which may be changed due to the diffusion of gases, in particular $CO_2$ into the sensing layer. Preferably, $CO_2$ may diffuse into the sensing layer and change the pH in said sending layer by interacting with water, thus increasing the concentration of protons and thus changing the pH.

The term "irradiated with a predetermined radiation" as used herein means that the sensing layer may be irradiated or excited with radiation of a suitable wavelength, in particular a wavelength which is able to generate an optical response of the sensing layer. For example, the irradiation may be carried out with visible light, infrared light and/or ultraviolet light. Preferred examples of a predetermined radiation is light of the green-blue visible spectrum, e.g. of a wavelength of about 400 to 500 nm, e.g. 440 nm, 450 nm, 460 nm, 470 nm, 480 nm, 490 nm etc. The radiation, i.e. the light wavelength as well its intensity, may in general be made dependent on or be adapted to the optically reactive material in the sensing layer. For specific optically reactive material suitable corresponding excitation wavelengths may be used.

Within the context of the chemo-optical sensor unit the sensing layer is adapted to measure an optical response of the at least one sensing layer, whose optical response depends on the concentration of the gas.

In a preferred embodiment, the sensing layer comprises as optically reactive material a luminescent material. The "luminescent material" may comprise one or more than one dye. The dye may be sensitive for the gas to be measured, e.g. for $CO_2$. The sensitivity may be indirect, for example, be provided via a sensitivity to pH, which in turn is influenced by gas, e.g. $CO_2$, that is diffusing into the sensing layer. Alternatively, the gas may itself have a direct influence on the sensitivity of the dye. In a particularly preferred embodiment, the luminescent material comprises two dyes. For example, the luminescent material may comprise a gas-sensitive dye which works as indicator dye, and a gas-insensitive dye which works as reference dye. In further embodiments, the two dyes as mentioned above may have different decay times. For example, the gas-sensitive dye may have a fast luminescence decay time, whereas the gas-insensitive dye may have a slow luminescence decay time. Examples of suitable reference dyes which are inert to a gas and which show a long decay time include: (1) transition metal complexes with ruthenium(II), rhenium (I), or osmium and iridium as central atom and diimine ligands; (2) phosphorescent porphyrins with platinum, palladium, lutetium or tin as central atom; (3) phosphorescent complexes of rare earths, for instance europium, dysprosium or terbium; and (4) phosphorescent crystals such as ruby, Cr-YAG, alexandrite, or phosphorescent mixed oxides such as magnesium fluoro-germanate. Examples of suitable indicator dyes which are sensitive to a gas and which show a short decay time include 8-Hydroxypyrene-1,3,6-trisulfonic acid, trisodium salt (HPTS), fluorescein, rhodamine B, rhodamine B-octadecyl ester, hexadecyl-acridine orange, hydroxymethyl coumarin, rhodamine, B-octadecyl ester, rhodamine B, naphthofluorescein, sulforhodamine 101, eosin, thionin, and Nile blue. In further specific embodiments, the present invention relates to combinations of reference dyes and indicators dyes, including all combinations of the above indicated exemplified indicators dyes and references dyes. Preferred examples of combinations of reference dyes and indicators dyes to be used in a chemo-optical sensor unit according to the invention include (reference dye/indicator dye): Ruthenium(II)-(tris-4, 7-diphenyl-1, 10-phenantroline)/HPTS; Ruthenium(II)-(tris-4, 7-diphenyl-1,10-phenantroline)/fluorescein; Ruthenium(II)-(tris-4, 7-diphenyl-1,10-phenantroline)/rhodamine B; Ruthenium(II)-(tris-4, 7-diphenyl-1,10-phenantroline)/rhodamine B-octadecyl ester; Ruthenium(II)-(tris-4,7-diphenyl-1,10-phenantroline)/hexadecyl-acridine orange; Europium (III)-tris-theonyl-trifluoromethyl acetonate/ hydroxymethyl coumarin; Platinum (II)-tetraphenylporphyrin/rhodamine B-octadecyl ester; Platinum (II)-tetraphenyl porphyrin/rhodamine B; Platinum (II)-tetraphenyl porphyrin/naphthofluorescein; Platinum (II)-tetraphenyl porphyrin/sulforhodamine 101; Platinum (II)-octaethyl porphyrin/eosin; Platinum (II)-octaethyl porphyrin/thionin; Platinum (II)-octaethyl ketoporphyrin/Nile blue; CR (III)-YAG/Nile blue; and Cr (III)-YAG/naphthofluorescein.

On the basis of a two dye combination in the sensor layer a measurement according to the Dual Lifetime Referencing principle, e.g. as derivable from U.S. Pat. No. 6,602,716 B1 or from Kocincova, New pH Sensitive Sensor Materials; Luminescent Fiber-Optic Dual Sensors for Non-Invasive and Simultaneous Measurement of pH and pO2 (Dissolved Oxygen) in Biological Systems, 2007, PhD thesis, University of Regensburg may be implemented. In particular, on the basis of the different decay times of the indicator and the reference dye, the intensity of the excitation may be modulated at a fixed frequency and the phase angle of the luminescence signal, which is independent of the amplitudes, may be detected and translated into a relative intensity of the gas-sensitive dye (indicator dye) from which subsequently the gas concentration may be determined.

Accordingly, the sensing layer may be at least passable for gas molecules such as $O_2$ and/or $CO_2$, which may arrive from a deeper layer such as the gas-permeable layer. Typically, the sensing layer may also be permeable for water molecules, which may diffuse in or out of deeper layers, i.e. layers below the sensing layer according to the osmotic pressure in the corresponding region of the chemo-optical sensor according to the present invention.

In certain specific embodiments, the sensing layer may comprise luminescent material which is capable of measuring the concentration of different gases, or which is capable of measuring the concentration of more than one gas simultaneously, e.g. the concentration of two gases at the same time. For example, the sensing layer may comprise two kinds of luminescent material adapted to the measurement of a different gas, respectively. Preferably, one sub-layer, region or one kind of material may be adapted to detect oxygen and a second sub-layer, region or kind of material is adapted to detect $CO_2$. Further details on multiparameter sensors and additional possibilities of implementing them would be known to the skilled person or can be derive from suitable literature sources such as WO 02/056023 or Schäferling, The Art of Fluorescence Imaging with Chemical Sensors, 2012, Angewandte Chemie International Edition, 51(15), 3532-3554.

The sensing layer may be provided as single layer. In alternative embodiments more than one sensing layer may be provided. Such second or further sensing layer may have the same properties or different properties than the first sensing layer. For example, the second or further sensing layer may comprise different luminescent material, e.g. different dyes, or it may be provided in a different chemical environment such as a different buffer, or having a different pH than a first sensing layer. In further embodiments, a second or subsequent sensing layer may be adapted to measure a different gas, than a first sensing layer, e.g. $O_2$ instead of $CO_2$ which may be measured in a first sensing layer.

The chemo-optical sensor unit may further be adapted to measure an optical response of the at least one sensing layer. Importantly, the received optical response is supposed to depend on the concentration of the gas to be measured. Such an adaption may comprise the provision of suitable detection methods or devices allowing to receive, detect and/or analyze one or more optical responses emanating from the sensing layer. The detection may be performed or implemented according to any suitable detection methods or on the basis of any suitable detection devices or comprising suitable components allowing to perform detection steps or sub-steps.

The term "gas-permeable layer" as used herein refers to a structure which is passable for gas molecules. Typically, the gas-permeable layer is provided as a membrane structure which is adapted to pass gas to the overlaying sensing layer. In specific embodiments, the gas-permeable layer is passable for gas molecules such as $O_2$ and/or $CO_2$. Typically, the gas-permeable layer may also be permeable for water molecules, which may diffuse in or out of layers above or below the gas-permeable layer, e.g. according to the osmotic pressure in the region of the chemo-optical sensor according to the present invention. Such diffusion process or transport of water molecules may, for example, be accomplished on the basis of water in the gas-phase.

The membrane of the gas-permeable layer may be composed of suitable gas and water permeable material. For example, the membrane may be a silicone membrane, or may comprise silicone. Alternatively, the membrane may be composed of or comprise materials such as PTFE (teflon) or derivatives. In further alternative embodiments, the membrane may be composed of or comprise a metal mesh, porous hydrophobic polymers, e.g. based on polypropylene and ethylene, porous hydrophobic silicon oxides such as areogels, or perfluoro materials such as nafion. Further suitable material would be known to the skilled person and are also envisaged in the context of the present invention.

The gas-permeable layer may further be composed of filler material which is passable for gas molecules. An example of such filler material is silicone rubber material. In a preferred embodiment, the gas-permeable layer may thus comprise silicone rubber or essentially consist of silicon rubber material.

In further preferred embodiments of the present invention, the gas-permeable layer may additionally be adapted to prevent light from passing through the gas-permeable layer. The term "preventing light from passing through the gas-permeable layer" is in particular intended to mean that the gas permeable layer is be adapted to reflect or scatter light transmitted through the at least one sensing layer, and/or to block possible light interferences outside of the intended sensor range. The reflection or scattering of light by the gas permeable layer may be achieved by using any suitable light reflecting material such as metals, e.g. aluminium, or metal oxides. Particularly preferred is the use of titanium compositions, e.g. compositions comprising $TiO_2$. In specific embodiments, the light reflection or scattering may be complete, i.e. for all wavelengths, or it may be specific for certain wavelengths or ranges of wavelengths. For example, light of a certain wavelength or range of wavelengths, in particular of the excitation wavelength for the luminescent material in the sensing layer, may be reflected or scattered, whereas light of a different wavelength which is not excitatory for the luminescent material in the sensing layer may not be reflected. In further embodiments, the light reflection or scattering may be dependent on specific parameters, e.g. temperature, pH, presence of gas molecules, presence of polar compounds etc. at the gas-permeable layer. Further, the gas permeable layer may block possible interference of fluorescent molecules, for example outside of the intended sensor range. In a preferred embodiment, the blocking of interference of fluorescent molecules may be a blocking of fluorescence outside of a range of about 400 nm-700 nm. Such a blocking activity may be accomplished by providing light absorbing materials, which work outside of the envisaged sensing range.

The gas-permeable layer may be provided as single layer. In alternative embodiments more than one gas-permeable layer may be provided. Such second or further gas-permeable layer may have the same properties as, or different properties than the first gas-permeable layer. For example, the second or further gas-permeable layer may have the property of reflecting light of a different wavelength. In further embodiments, the second or further gas-permeable layer may have the property of being permeable for different molecules than the first gas-permeable layer. E.g. different gases, or different compounds may pass through the first and second or subsequent gas-permeable layer. In further specific embodiments of the invention the chemo-optical sensor may further comprise at least one optical transparent layer adjacent to the at least one sensing layer. The optical transparent layer may preferably be on top of the sensing layer, which in turn is on top of the gas-permeable layer as defined herein above. The transparent layer may accordingly cover the sensing layer and protect it from direct contact with the surrounding atmosphere. Thus, the at least one sensing layer may be enclosed by the gas permeable layer from one side and by the optical transparent layer from the other side. The term "optical transparent layer" as used herein refers to a carrier substrate which is at least partially transparent for radiation. In some embodiments, the optically transparent layer may be transparent for the entire suitable spectrum of electromagnetic waves, e.g. infrared light, visible light and ultraviolet light. In other embodiments, the optically transparent layer may be transparent for specific wavelengths or wavelength ranges only. The optical transparent layer may for example be transparent for the predetermined radiation as described above, or excitation wavelength(s) or wavelengths range(s) for the luminescent material(s) in the sensing layer, whereas light of a different wavelength which is not excitatory for the luminescent material in the sensing layer may not be passed. In addition, the optical transparent layer may be transparent for the light of the optical response generated in the sensing layer. Such light may be provided in a specific wavelength or range of wavelength which may specifically be passed through the optical transparent layer, whereas light of different wavelengths may be passed. In a specific embodiment, the optical transparent layer may only be transparent for excitation wavelength(s) or ranges of wavelength(s) for the luminescent material in the sensing layer and for the wavelength(s) or range of wavelength(s) generated as optical response by said luminescent material in the sensing layer The optical transparent layer may be composed of any suitable transparent material known to the skilled person. The optical transparent layer may, for example, be composed of transparent material such as glass, polycarbonate, PET, silicone rubber, or PMMA (plexiglas).

In further embodiments, the optical transparent layer may be non-permeable for gas, e.g. for $O_2$ and/or $CO_2$.

In a central aspect the present invention provides a chemo-optical sensor unit as defined herein which is adapted to operate with a contact medium between the gas-permeable layer and the skin. The term "contact medium" as used herein refers to a medium which may be provided at the interface between the chemo-optical sensor unit and the surface layer on which the measurement of gas is to be carried out, i.e. the skin. Preferably, the contact medium is interposed at least between the gas-permeable layer as defined herein above and the surface layer on which the measurement of gas is to be carried out, i.e. the skin of the human or animal body. The contact medium may be a gel, or liquid, which typically allows to transfer gas molecules from the deeper layer, e.g. skin, to the chemo-optical sensor unit according to the present invention. Thus, in a particularly preferred embodiment, the contact medium is at least gas-permeable. The gas-permeability may be a general permeability for any gaseous material. Alternatively, the contact medium may have a specific permeability for certain gas molecules, e.g. for $O_2$, $CO_2$, CO, $N_2$, or $NH_3$. Particularly preferred is the permeability for $O_2$ and/or $CO_2$. Most preferred is the permeability for $CO_2$. In specific embodiments, the contact medium may be selectively permeable for certain gases and impermeable for other gases. It is preferred that the contact medium by selectively permeable for at least $O_2$ and/or $CO_2$. Most preferred is a selective permeability for $CO_2$.

Furthermore, the contact medium may allow to keep the water content or moisture content of the surface layer on which the measurement of gas is to be carried out stable, or to control the water content or moisture content of the surface layer on which the measurement of gas is to be carried out, e.g. the skin of the human or animal body. Advantageously, the contact medium may comprise a barrier-layer which is gas-permeable and which is at the same time impermeable to liquid water and ions. The contact medium may accordingly provide such a barrier layer, which may be placed between the skin and the chemo-optical sensor and may thereby avoid the transport of liquid water from the skin or the contact medium itself to the chemo-optical sensor, or from said sensor to the contact medium or the skin. Typically, the barrier layer may not comprise liquid water or any aqueous solution.

The barrier layer may be provided as a single layer structure, or as multilayer structure. In case of a multilayer structure, 2, 3, 4, 5, 6 or more layers may be present, which may be either identical or be different, e.g. with respect to their chemical constituents, their thickness, their gas permeability, or their permeability for water. For example, in case 2 or 3 layers are used, it is envisaged that at least one of these layer is impermeable for water and ions. Further layer may have a reduced permeability for water and ions, or may be provided for structural reasons and accordingly be permeable for water and ions. The contact medium is, in further embodiments, characterized as being biocompatible. The term "biocompatible" as used herein means that the contact medium does not cause a toxic, immunologic, and/or allergic reaction to the surface area of the skin of the human or animal body to which it is applied, or to the body of the person to which it is applied, or any other biologically or medicinal deleterious or harmful reaction, e.g. that it is not carcinogenic.

In addition, the contact medium may be thermally conductive. The thermal conductivity may be used to mitigate thermal changes of the chemo-optical sensor unit, i.e. to minimize a temperature difference between the chemo-optical sensor and the skin area underlying the contact medium. Thereby a constant temperature at the chemo-optical sensor unit can be achieved, thus allowing for an accurate measurement of the concentration of a gas.

In an embodiment the present invention provides a chemo-optical sensor unit as defined herein which is provided together with a contact medium comprising said barrier layer as defined herein above or below. The provision may be, for example, a packaging, storing, keeping, suspending of the chemo-optical sensor together with the contact medium.

In a particularly preferred embodiment, the contact medium and/or the conditioning fluid comprises at least a hydrophobic compound. A "hydrophobic compound" as used herein means any compound, which repels water or aqueous solutions comprising water and dissolved entities such as ions. The hydrophobic compound may be any hydrophobic compound known to the skilled person including crude oil derivates, alkanes, oils, fats, silicon based materials, fluor based materials such as fluorocarbons etc.

In a preferred embodiment, the hydrophobic compound is a hydrophobic liquid. Such hydrophobic liquid may, for example, be an oil. Preferred examples of oils are hydrocarbon containing oils, silicon containing oils or fluor containing oils, e.g. fluorocarbon oils.

Particularly preferred is the use of edible oils or waxes. Examples of edible oils envisaged by the present invention are cotton seed oil, linseed oil, cameline oil, corn oil, rapeseed oil, poppy-seed oil, peanut oil, soja oil, hazel-nut oil, walnut oil, almond oil, argan oil, olive oil, safflower oil, sunflower oil, sesame oil, coconut oil/wax, butter, cocoa butter, lard or mustard oil. Also preferred is the use of non-edible waxes and oils from crude oil or animals. An example of such compound is lanoline. Also envisaged is the use of low melting waxes or fats. Preferred is the use of low melting edible waxes. Examples of such waxes include butter or cocoa butter. Particularly preferred is the use of sunflower oil.

In further embodiments, the hydrophobic compound in the contact medium is a diorganosilicon. Examples of suitable organosilicons compounds contain groups like silanols, siloxides, or silyl ethers. Further envisaged is the use of siloxanes, in particular non-volatile siloxanes. Also within the scope of the present invention is the use of volatile siloxanes. In case such volatile siloxanes are used, the usage time may be limited according to the evaporation rate of the compound. In further embodiments, a mixture of volatile and non-volatile siloxanes may be used. Suitable siloxanes may be a methyl phenyl siloxane or a dimethylsiloxaneFurther examples of suitable siloxanes inlcude hexamethylcyclotrisiloxane, octamethylcyclotetrasiloxane, octamethyltrisiloxane, decamethylcyclopentasiloxane, decamethyltetrasiloxane, dodecamethylcyclohexasiloxane. Also envisaged is the use of silicones designed for cosmetics, e.g. Belsil silicones manufactured by Wacker. The use of any further suitable siloxanes or silicones, which would be known to the skilled person, is also envisaged in the context of the present invention.

In further embodiments, the hydrophobic compound is a siloxane oil, e.g. a diorganopolysiloxane. A preferred example of siloxane oil is polydimethylsiloxane, polymethylphenylsiloxane or any derivative thereof. In specific embodiments, a non-volatile polydimethylsiloxane may be used in combination with a volatile siloxane, prefarbly comprising within the combination at least one of the following compounds: hexamethylcyclotrisiloxane, octamethylcyclotetrasiloxane, octamethyltrisiloxane, decamethylcyclopentasiloxane, decamethyltetrasiloxane, or dodecamethylcyclohexasiloxane.

In further preferred embodiments, the hydrophobic compound is a soft silicone rubber or a gel. The term "soft silicone rubber or gel" as used herein refers to an elastomeric silicone-polymer comprising silicon, carbon, hydrogen and oxygen and a shore A value (stiffness value) of smaller than 40. Silicon rubbers may be produced according to any suitable methodology known to the skilled person. In further preferred embodiments, the hydrophobic compound is a perfluoroalkane oil. Examples of suitable perfluoroalkane oils include perfluoro octyl bromide, perfluorodecalin, perfluoro tributylamine, perfluoro t-butylhexane and FC-75.

Further, the hydrophobic compound may be a soft perfluoro rubber such as FFKM. Also envisages is the use of Teflon, i.e. of FEP.

Further envisaged is the possibility to use any combination of the above mentioned compounds or compound categories, or the presence of any combination of these compounds as described herein above in the contact medium.

Particularly preferred is the employment of perfluoro oils, either alone or in combination with any of the other mentioned compounds or categories of compounds. Also preferred is the use of silicone oils, crude oil paraffins and edible oils, either alone or in combination with any of the other mentioned compounds or categories of compounds.

The contact medium as defined herein thus advantageously provides the functionality of a balancing means between the chemo-optical sensor unit and the underlying surface, e.g. skin surface, facilitating gas exchange and avoiding chemical or osmotic molecular perturbations in the chemo-optical sensor unit. By providing a hydrophobic compound as barrier layer in the contact medium, the osmotic environment inside and outside of the chemo-optical sensor unit (at least with respect to the surface to be analysed, i.e. below the chemo-optical sensor unit) becomes undisturbed. It is accordingly possible detecting the concentration of gas in the skin without compromising the sensitivity of the method due to water transport in the sensor unit or out of the sensor. This advantageously helps avoiding calibration or recalibration steps during the use of the chemo-optical sensor unit.

The above mentioned first hydrophobic compound may be provided in any suitable concentration in the contact medium. For example, an edible oil such as olive oil or any other of the mentioned oils, rubbers or hydrophobic compounds may be provided in an amount of 10%, 15%, 20%, 25%, 30%, 35%, 36%, 37%, 38%, 39%, 40%, 45%, 50%, 55%, 60%, 65%, 70%, 75%, 80%, 85% by volume of the contact medium.

In a further preferred embodiment, the barrier layer may be provided in any suitable thickness. For example, the layer may have a thickness of about 3 to 15 nm, e.g. about 5 nm. It is preferred that the barrier layer is a thin layer with a thickness at the lower limit.

In a specific embodiment, the barrier layer may be present in said contact medium in such a thickness that the optical response of the chemo-optical sensor unit when being in contact with the said contact medium is stable when said chemo-optical sensor unit is employed on the skin. The barrier layer comprising a hydrophobic compound as defined herein thus advantageously provides the functionality of a balancing means between the chemo-optical sensor unit, the contact medium and the underlying surface, e.g. skin surface, facilitating gas exchange and avoiding chemical or osmotic perturbations due molecular perturbations such as movement of water out of the chemo-optical sensor unit and/or in or out of the surface layer to be analysed, i.e. skin surface. It is accordingly possible detecting the concentration of gas in the skin without compromising the sensitivity of the method due to molecular perturbations in the chemo-optical sensor unit. As a result the detectable optical response is received in a stable manner, which does not alter due to molecular perturbations such as water transport etc. The stability of the response may, for example, be tested with a device as described herein. In further embodiments, the stability may be tested by sampling from a batch and by an in vitro testing. Such a test may, for example, comprise the exposure of the sensor to a fixed $CO_2$ concentration induced in a contact medium, e.g. as described herein.

In a further embodiment the chemo-optical sensor of the present invention comprises or includes a contact medium as defined herein above, or consists of a combination of the elements of the chemo-optical sensor mentioned herein above, e.g. at least one sensing layer and at least one gas-permeable layer, and a contact medium as defined herein above.

The chemo-optical sensor according to the present invention is suitable for transcutaneous measurement. The chemo-optical sensor unit may, in specific embodiments, also be used for different measurement purposes, e.g. in the context of microbiological or biotechnological production processes. Preferably, the chemo-optical sensor unit is a transcutaneous sensor unit. The term "transcutaneous sensor unit" as used herein means that the sensor is to be applied or can be applied on the skin. Accordingly, the sensor is capable of measuring blood gas concentrations of a subject via the subject's skin, wherein blood gas may diffuse via the skin into the chemo-optical sensor unit passing a contact medium as defined herein above. The term "blood gas" as used herein refers to gaseous materials present in the blood and capable of exiting a body, which can be measured, e.g. over the skin. The measurement is such that a chemically exact reflection of the gas content of blood is obtainable. The preferred blood gas concentrations to be measured are the concentrations of $O_2$ or $CO_2$. Particularly preferred is the measurement of the concentration of $CO_2$.

In another embodiment of the present invention, the chemo-optical sensor unit as defined herein above may comprise additional components or be combined with additional components.

For example, the chemo-optical sensor may be combined with or comprise at least one light source which is adapted to irradiate the sensing layer as defined herein above. The light source may provide radiation in a predetermined wavelength, preferably light in an excitation wavelength or range of wavelengths adapted to the dye or dyes present in the sensing layer. The light source may have any suitable form, provide any suitable intensity and provide any suitable wavelength(s). The light source may preferably be a light emitting diode (LED).

In a further optional embodiment, the light source may additionally be combined with a light guiding structure. The light guiding structure may be arranged, for example, above the sensing layer/optically transparent layer of the chemo-optical sensor and may be connected to a light source external to the chemo-optical sensor unit, e.g. as defined above. Light from an external light source may be introduced into the light guiding structure, which is adapted to direct said light towards the at least one sensing layer. The light-guiding structure may comprise any suitable light guiding material. Preferably, optical fibers may be used as light guiding material, which may be provided in the form of light-guiding structures. Optical fibers may accordingly be provided as single fibers, or as fiber bundles. A light source, being connected to a light guiding structure, may thus be used to irradiate the sensing layer of a chemo-optical sensor unit according to the present invention, although being located externally. In further embodiments, a light source may be connected to more than one chemo-optical sensor unit via light guiding structures arriving at distinct sensor units.

The chemo-optical sensor may further be combined with a detection device. Such a detection device, for instance a photosensitive device, may be capable of sensing an optical response coming from the sensing layer and may be adapted to generate signals, e.g. electrical signals, corresponding to the sensed optical response. The signals may further be transmitted to an external apparatus for subsequent analysis. The detection device may be adapted to the optical response expected from the sensing layer, e.g. provided by a dye or a combination of dyes as described herein above.

The detection device may further be combined via a light guiding structure to the chemo-optical sensor unit as defined herein. In specific embodiments the same light guiding structure, which provides light from the light source to the sensing layer, may be used to collect the optical response of the sensing layer and to guide said optical response, for instance fluorescent light, via the same or a different optical fiber to a detection device or an apparatus external to the chemo-optical sensor unit for analysis. By using light guiding structures it is thus possible to connect an input and/or output light guiding structure, which is/are coupled to the chemo-optical sensor unit. In this embodiment no additional unit needs to be connected to the chemo-optical sensor unit accommodating the light source and the at least one detection device.

In specific embodiments, the light may thus be transferred into the sensing layer and luminescence, e.g. fluorescence light, may be collected through the same surface of the sensing layer. Alternatively, a light guiding structure connected, for example, via optical fibers to a light source which may be external to the chemo-optical sensor unit, may be used to direct light from an external light source and transmitted through at least one optical fiber towards the at least one sensing layer. At least one detection device, for instance a photosensitive device, may then be included to sense an optical response and may be adapted to generate e.g. electrical signals corresponding to the sensed optical response. Said signals may be transmitted to an external device for analysis. Alternatively, the chemo-optical sensor unit may be adapted to perform said analysis and to output the analysis results to some external device.

Preferably, the at least one light source and the at least one detection device may form a unit. This unit may in a further preferred embodiment be detachably connected to the chemo-optical sensor unit, e.g. by a housing or structure. Accordingly, certain parts of the chemo-optical sensor unit, for instance the sensing layer, gas permeable layer, or a housing and/or supporting structure of the chemo-optical sensor unit may be disposable, whereas other parts of the optical sensor such as the light source and the detection device, or the light guiding structures and may be reused. This reduces costs, since expensive parts such as light sources and/or detection devices and/or electronics do not have to be replaced and can be reused.

In specific embodiment, the chemo-optical sensor unit may be composed of two devices or two parts, a disposable or cartridge part and a non-disposable or reusable part. In particular, the disposable or cartridge part may work as passive device and not include any expensive electronics at all. Hence, this part may be manufactured with low effort thereby reducing costs, whereas the second, non-disposable part may include the electronics or optical elements and be reused. It may accordingly also be uses with different disposable parts, e.g. allowing to measure the concentration of different gases (for instance $O_2$ and $CO_2$). Thereby an increased flexibility of the chemo-optical sensor unit can be provided.

Another example of an additional component, which may be combined with the chemo-optical sensor as described above is at least one heating element. Additionally, or alternatively, the chemo-optical sensor may comprise at least one temperature sensor. If, for example, the chemo-optical sensor unit is attached to a person's skin, the heating element may be adapted to increase blood perfusion and gas permeability of the skin, thereby increasing sensitivity and accuracy of the chemo-optical sensor unit, in particular its transcutaneous application. The heating element may be in any suitable form, e.g. could be in the form of a diode or may comprise a thin foil to minimize optical distances and thermal mass. Alternatively, the heating element may be a resistance heater or diode so that the heating element can also be used as a temperature sensor, i.e. heating element and temperature sensor are formed by the same device. This advantageously may reduce costs and space required for installation of a heater and temperature sensor. In further embodiments, the temperature sensor may be realized as a separate element for sensing the temperature of the chemo-optical sensor unit, e.g. in order to avoid injuries or burnings of the skin. During operation the temperature of the heating element and of the contact medium and sensing layer may be increased by the heating element to a temperature in the range of 42° to 45° C. This temperature range may increase capillary blood flow in the skin and bring the capillary blood gas levels close to the arterial blood gas levels. During operation the sensor temperature may accordingly be measured by at least one temperature sensor as defined above, included in the heating element and/or the contact element and/or by a separately provided temperature sensor. The temperature may be controlled such as to have a well defined measurement condition and to prevent burning of the skin.

In further specific embodiments, temperature sensors and/or heating elements may be provided as non-disposable or reusable parts of the chemo-optical sensor unit. The temperature sensors and/or heating elements may accordingly be detachably connected to other elements of the chemo-optical sensor unit as defined herein above.

In another aspect the present invention relates to a system relates to a system for patient monitoring and/or ventilation of a patient, comprising a chemo-optical sensor unit as defined herein above, a ventilation device and/or a monitoring device.

The monitoring device may, for example, include opto-electronics for supplying the chemo-optical sensor unit with light via optical fibers, and for receiving luminescent light from the sensing layer. The monitoring device may further comprise means for determining/calculating a gas concentration based on the received optical response, for instance light intensity of the luminescent light generated in the sensing layer. The monitoring device may further comprise a heater controller for controlling the temperature of the heating element. The heater controller may be adapted for detecting the temperature of the heating element using the temperature sensor included in the chemo-optical sensor unit and for adjusting for instance a current flowing through a resistance heater included in the heating element or the contact element based on the detected temperature. The monitoring device may additionally comprise means for communication with the ventilation device. Said communication means may include at least one communication technique, e.g. wired (cable), wireless (Bluetooth, infrared, RF), etc. In a preferred embodiment, the monitoring device comprises means for calculating/determining the gas concentration, in particular $O_2$ and most preferably $CO_2$, from the measured/sensed optical response of the sensing layer, for instance from the sensed intensity or decay time of the luminescent light. The analyzing device, e.g. monitoring device, may be based on the operation of an algorithm that may also be adapted to compensate, inter alia, for temperature effects for calculating/determining the gas concentration may use.

The ventilation device may include all functions associated of a typical ventilation device for invasive or non-invasive ventilation of a patient with respiratory failure. The ventilation device may, for example, comprise display means and a storage device for displaying and storing information/data received from the monitoring device. In particular, the display means of the ventilation device may be adapted to display a gas concentration, e.g. $O_2$ or $CO_2$, determined by the monitoring device and may further store gas concentration information over a predetermined time period for instance for later evaluation by a physician or for close loop adaptation of the ventilation settings. In another embodiment, the ventilation device may be controlled on the basis of the measured/determined concentration of gas.

In specific embodiments the chemo-optical sensor unit may be operationally coupled to a monitoring device and/or a ventilation device as defined herein above, wherein the monitoring device may be adapted to at least one of analyzing the optical response of the sensing layer, controlling the heating element and/or the temperature sensor, or displaying the determined gas concentrations, etc. The monitoring device or ventilation device may additionally include means for storing monitored data, e.g. as a function of time. These data can be made available at a later time for analysis by a physician, e.g. by transfer to a hospital computer system, or a physician's handheld diagnosis apparatus.

In yet another aspect the present invention relates to a method for conditioning a chemo-optical sensor unit for transcutaneous measurement of a concentration of a gas, comprising: at least one sensing layer adapted to be irradiated with a predetermined radiation; and at least one gas-permeable layer adjacent to one side of the at least one sensing layer, adapted to pass gas whose concentration is to be measured through the gas-permeable layer towards the sensing layer; wherein said chemo-optical sensor unit is adapted to operate with a contact medium between the gas-permeable layer and the skin, wherein said contact medium comprises a barrier layer which is gas-permeable and impermeable to water and ions; and wherein the chemo-optical sensor unit is adapted to measure an optical response of the at least one sensing layer, whose optical response depends on the concentration of the gas, the method comprising contacting said chemo-optical sensor unit with a contact medium comprising a barrier layer which is gas-permeable and impermeable to water and ions. It is preferred that the contact medium is a contact medium as defined herein above, i.e. a contact medium comprising a barrier layer such a s barrier layer comprising a hydrophobic compound.

The term "contacting" as used in the context of the method described above refers to an application of said contact medium directly onto the chemo-optical unit, e.g. by placing it on the sensor unit. Also envisaged is the provision of the contact medium in the form of an adhesive or adhesive-like structure which may be adhered or sticked to the sensor unit.

In a further aspect the present invention relates to a chemo-optical sensor unit obtainable by a method for conditioning the chemo-optical sensor unit as defined herein above. The accordingly obtained chemo-optical sensor unit may be regarded as being conditioned and thus directly usable for the transcutaneous measurements without previous calibration. Such a chemo-optical sensor unit may further be combined with further components such a light source or a detection device as described herein above, or it may be provided in the form of a system for patient monitoring as defined herein above. In further specific embodiments, the chemo-optical sensor may be provided as such or be provided with or comprise a contact medium as defined herein above, or the chemo-optical sensor may be provided with a conditioning fluid as defined herein above.

The following example and figures are provided for illustrative purposes. It is thus understood that the example and figures are not to be construed as limiting. The skilled person in the art will clearly be able to envisage further modifications of the principles laid out herein.

EXAMPLES

Example 1—Effect of Perfluorooctylbromide Studied in a Transcutaneous Situation

In an experiment the effect of perfluorooctylbromide in a transcutaneous measurement is studied. A dedicated sensor probe comprising a PreSens spot and a commercial Radiometer TOSCA transcutaneous $PtcCO_2/SpO_2$ probe for referencing are both placed on the under-arm of a test-person. Both sensors are heated up to 45° C. and 3 ml of perfluorooctylbromide is placed between the sensor and the skin. Prior to the measurement, the PreSens spot is pre-conditioned in a Physiological Saline solution (9 g/l NaCl).

The perfluorooctylbromide will stop the permeation of water from the skin to the sensor while the moisturizing behavior of perfluorooctylbromide will keep water in the skin. The response stabilizes to a much lower, but fairly constant, cutaneous $pCO_2$ level compared to the reference sensor.

The actual sensitivity reduction is not well defined because it will depend on for instance the volume of perfluorooctylbromide between sensor spot and skin.

The invention claimed is:

1. A chemo-optical sensor unit for transcutaneous measurement of a concentration of a gas, comprising:
   at least one sensing layer adapted to be irradiated with a predetermined radiation;
   at least one gas-permeable layer adjacent to one side of the at least one sensing layer and adapted to pass gas whose concentration is to be measured through the at least one gas-permeable layer towards the at least one sensing layer;
   a contact medium configured to be positioned between the at least one gas-permeable layer and skin, wherein the contact medium comprises a barrier layer which is gas-permeable and impermeable to water and ions; and
   at least one photosensitive detector adapted to measure an optical response of the at least one sensing layer to the predetermined radiation, wherein the optical response depends on the concentration of the gas.

2. The chemo-optical sensor unit of claim 1, wherein the contact medium is at least one of biocompatible and thermally conductive.

3. The chemo-optical sensor unit of claim 1, wherein the barrier layer comprises a hydrophobic compound.

4. The chemo-optical sensor unit of claim 3, wherein the hydrophobic compound is a hydrophobic liquid.

5. The chemo-optical sensor unit of claim 4, wherein the hydrophobic compound or the hydrophobic liquid is a hydrocarbon, fluor or silicon containing oil, an organosilicone, a soft rubber, or a gel.

6. The chemo-optical sensor unit of claim 5, wherein:
   the hydrophobic liquid is an edible oil, a low melting edible wax, a crude oil derivate, a silicone oil, a silicone wax, or a perfluoro oil;
   the low melting edible wax is cocao butter; and
   the crude oil derivate is a paraffin oil or a soft paraffin wax.

7. The chemo-optical sensor unit of claim 1, wherein the at least one gas-permeable layer and/or the at least one sensing layer comprises a silicon rubber.

8. The chemo-optical sensor unit of claim 1, wherein the barrier layer has a thickness such that the optical response is stable when the chemo-optical sensor unit is in contact with the contact medium having a constant gas concentration.

9. The chemo-optical sensor of claim 1, wherein the at least one sensing layer comprises luminescent material and wherein the at least one gas-permeable layer is adapted to prevent light from passing through the at least one gas-permeable layer.

10. The chemo-optical sensor of claim 1, wherein:
the chemo-optical sensor is a transcutaneous sensor unit for measuring blood gas concentration; and
the blood gas concentration corresponds to a gas concentration of $O_2$ and/or a gas concentration of $CO_2$.

11. The chemo-optical sensor unit of claim 1, further comprising:
at least one light source adapted to irradiate the at least one sensing layer; and
a light guiding structure connected to the at least one light source, wherein the light guiding structure is connected to the at least one photosensitive detector, and wherein at least one of: the at least one light source, the light guiding structure, and the at least one photosensitive detector are detachably connected to the chemo-optical sensor unit.

12. The chemo-optical sensor unit of claim 1, wherein the barrier layer comprises a plurality of layers, and wherein each of the plurality of layers has one of: a same chemical constituency or a different chemical constituency.

13. The chemo-optical sensor unit of claim 12, wherein each of the plurality of layers has the different chemical constituency, at least one of the plurality of layers is impermeable to water or ions and at least another of the plurality of layers has a reduced permeability to water or ions with respect to the at least one of the plurality of layers.

14. The chemo-optical sensor unit of claim 1, wherein the at least one photosensitive detector comprises a photosensitive device configured to sense the optical response and generate electrical signals corresponding to the optical response.

15. A system for patient monitoring and/or ventilation of a patient, comprising:
a chemo-optical sensor unit, comprising:
at least one sensing layer adapted to be irradiated with a predetermined radiation;
at least one gas-permeable layer adjacent to one side of the at least one sensing layer and adapted to pass gas whose concentration is to be measured through the at least one gas-permeable layer towards the at least one sensing layer, wherein:
a contact medium configured to be positioned between the at least one gas permeable layer and skin, wherein the contact medium comprises a barrier layer which is gas-permeable and impermeable to water and ions; and
at least one photosensitive detector adapted to measure an optical response of the at least one sensing layer to the radiation, wherein the optical response depends on the concentration of the gas; and
at least one of: a ventilation device and
a monitoring device.

16. A method for conditioning a chemo-optical sensor unit for transcutaneous measurement of a concentration of a gas, comprising:
contacting the chemo-optical sensor unit with a contact medium comprising a barrier layer which is gas-permeable and impermeable to water and ions;
irradiating at least one sensing layer of the chemo-optical sensor unit with a predetermined radiation;
measuring a concentration of a gas adapted to pass through at least one gas-permeable layer of the chemo-optical sensor unit adjacent to one side of the at least one sensing layer, towards the at least one sensing layer, wherein the concentration of the gas is to be measured through the at least one gas-permeable layer, and wherein the chemo-optical sensor unit is adapted to operate with the contact medium is configured to be positioned between the at least one gas-permeable layer and skin; and
measuring an optical response of the at least one sensing layer to the predetermined radiation using at least one photosensitive detector, wherein the optical response depends on the concentration of the gas.

17. The method of claim 16, wherein the contact medium is at least one of biocompatible and thermally conductive.

* * * * *